United States Patent [19]
Hartenstein et al.

[11] 3,936,438
[45] Feb. 3, 1976

[54] AROMATIC CARDENOLIDE ACETALS

[75] Inventors: Hartenstein, Wittental; Gerhard Satzinger, Denzlingen; Manfred Herrmann, Saint Peter, all of Germany

[73] Assignee: Warner-Lambert Company, Morris Plains, N.J.

[22] Filed: Sept. 27, 1974

[21] Appl. No.: 509,752

[30] Foreign Application Priority Data
Oct. 8, 1973 Germany............................ 2350392

[52] U.S. Cl................................. 260/210.5; 424/182
[51] Int. Cl.².......................................... C07J 173/00
[58] Field of Search.................................. 260/210.5

[56] References Cited
UNITED STATES PATENTS

| | | | |
|---|---|---|---|
| 3,752,807 | 8/1973 | Hartenstein et al. | 260/210.5 |
| 3,783,149 | 1/1974 | Heider et al. | 260/210.5 |

Primary Examiner—Johnnie R. Brown
Assistant Examiner—Cary Owens
Attorney, Agent, or Firm—Albert H. Graddis; Frank S. Chow; George M. Yahwak

[57] ABSTRACT

The present invention is concerned with new cardenolide acetals of the general formula:

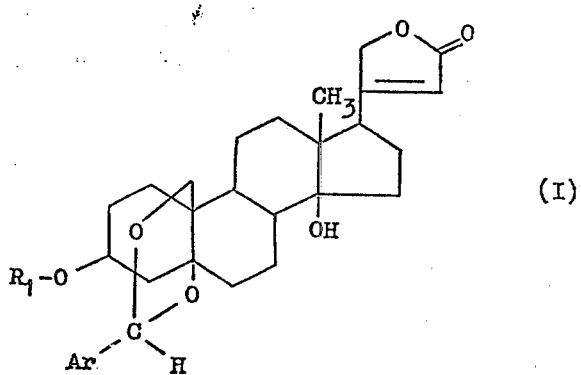

wherein $R_1$ is an unsubstituted or substituted glycosyl radical and Ar is an unsubstituted or substituted aryl or heteroaryl radical and with the preparation thereof. These compounds exert a positive inotropic action on the cardiac muscle of mammals.

34 Claims, No Drawings

AROMATIC CARDENOLIDE ACETALS

The cardenolide glycosides are well established in the therapy of cardiac insufficiency. Although some of the individual glycosides show considerable differences, a common feature of all of them is a comparatively narrow therapeutic spectrum, i.e. the therapeutic dose is close to the toxic dose. The result of this is that serious toxic phenomena frequently occur, in the case of imprecise dosage, over-dosing or in the case of reduced glycoside tolerance.

It is an object of the present invention to provide cardiac-active glycosides which have an improved therapeutic safety.

From U.S. Pat. No. 3,752,807, it is admittedly known that 5β,19-isopropylidene-cardenolide acetals are characterized by an especially good enteral effectiveness but, in spite of certain advantages in comparison with the longer-known cardiac glycosides, the problem of a narrow therapeutic spectrum is not satisfactorily solved by the availability of these compounds.

We have now found that the compounds of general formula (I):

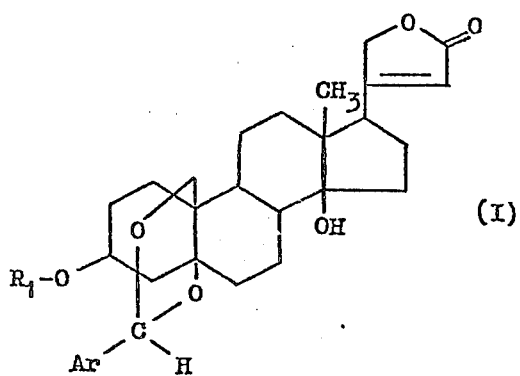

wherein $R_1$ is an unsubstituted or substituted glycosyl radical and Ar is an unsubstituted or substituted aryl or heteroaryl radical, not only possess an outstanding enteral effectiveness, but that the therapeutic spectrum is substantially widened by the introduction of an aromatic acetal grouping in the genin core. There are thus provided, for the therapy of cardiac insufficiency, enterally highly effective substances which have an especially high therapeutic safety. Furthermore, the new compounds according to the present invention possess an excellent chemical stability so that in this regard, they also represent a considerable advance over the prior art.

Since the present invention depends essentially upon a structural alteration of the genin of known cardiac glycosides, as glycosyl radicals there can be considered all the previously used sugar residues, for example, the digitoxosyl, rhamnosyl, glucosyl, mannosyl, galactosyl, cymarosyl, boivinosyl, oleandrosyl, thevetosyl and acofriosyl radicals, the hydroxyl groups of which can be replaced wholly or partially by lower alkoxy, acyloxy or alkoxyalkoxy radicals or wherein adjacent hydroxyl groups can also be jointly acetalised or ketalised by lower isoalkylidene, cycloalkylidene or alkoxyalkylidene radicals.

As lower alkoxy, acyloxy and alkoxyalkoxy radicals and as lower isoalkylidene or alkoxyalkylidene radicals, there are to be understood radicals with up to 8 and preferably up to 4 carbon atoms, for example, methoxy, ethoxy, propoxy, isopropoxy, butoxy, octyloxy, acetoxy, propionyloxy, butyryloxy, heptanoyloxy, methoxymethoxy, ethoxymethoxy, butoxyethoxy, propoxypropoxy, ethoxybutoxy, isopropylidene, isobutylidene, methoxyisopropylidene, propoxyisopropylidene and ethoxyisobutylidene radicals. Preferred radicals in the sugar molecule include, for example, methyl, ethyl, acetyl, isopropylidene, cyclopentylidene and cyclohexylidene radicals. As cycloalkylidene radicals, there can be used those with a carbocyclic ring containing 5 to 7 and preferably 6 carbon atoms.

Those compounds of general formula (I) are preferred in which $R_1$ is a digitoxosyl radical of the general formula:

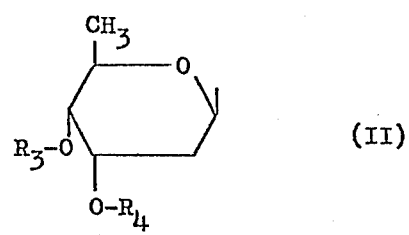

wherein one of the symbols $R_3$ and $R_4$ represents a hydrogen atom and the other one a hydrogen atom or a methyl radical or an acyl radical containing up to 4 carbon atoms or wherein the symbols $R_3$ and $R_4$ together also represent an isopropylidene or lower alkoxymethylene radical.

Also preferred are those compounds of general formula (I) in which $R_1$ is a rhamnosyl radical of the general formula:

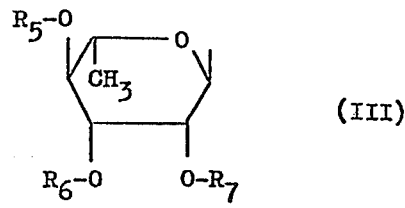

wherein the symbols $R_5$, $R_6$ and $R_7$ represent hydrogen atoms or one of the symbols $R_5$, $R_6$ and $R_7$ can also represent a methyl radical or an acyl radical containing up to 4 carbon atoms or $R_6$ and $R_7$ can together represent an isopropylidene, cyclohexylidene or lower alkoxymethylene radical.

Of the rhamnosyl radicals of general formula (III), those are particularly preferred in which the symbol $R_5$ or $R_6$ represents a methyl radical or the symbols $R_5$ and $R_7$ represent acyl radicals containing up to 4 carbon atoms.

By unsubstituted and substituted aryl and heteroaryl radicals, there are to be understood those radicals which are derived from compounds of an aromatic character, for example, the phenyl, furyl, thienyl and pyridyl radicals, which can be substituted by, for example, halogen atoms or alkyl or alkoxy radicals containing up to 3 carbon atoms, as well as by trifluoromethyl radicals or methylenedioxy or ethylenedioxy radicals. The preferred radicals are phenyl radicals which can be unsubstituted or substituted by fluorine, chlorine, bromine, methoxy, ethoxy, methyl, ethyl, propyl, isopropyl, trifluoromethyl, methylenedioxy or ethylenedioxy radicals. The most preferred compound according to the present invention is 5,19-benzylidene-cymarol.

The new compounds of general formula (I) according to the present invention can be prepared by reacting a compound of the general formula:

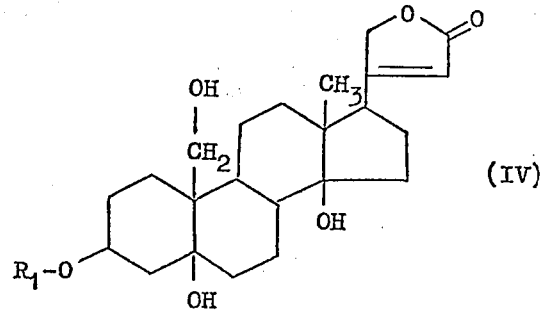

wherein $R_1$ has the same meaning as above, with an excess of a dialkylacetal of the general formula:

wherein Ar has the same meaning as above and $R_2$ is a lower alkyl radical, in the presence of an acidic catalyst, at a temperature between $-15°C$. and the boiling temperature of the reaction mixture and preferably at ambient temperature.

The reaction is preferably carried out in an inert organic solvent at ambient temperature.

The lower alkyl radical $R_2$ of general formula (V) is preferably a methyl, ethyl or propyl radical.

As inert solvent, there is preferably used an aprotic solvent, for example, chloroform, dioxan, tetrahydrofuran or dimethyl formamide. As reaction medium, there can also be used the aldehyde corresponding to the acetal used.

As acidic catalysts, there can be used inorganic or strong organic acids, for example, ethereal hydrogen chloride, concentrated sulphuric acid, 70% perchloric acid, methane-sulphonic acid, p-toluene-sulphonic acid or sulphonic acids in the form of ion exchanger resins, for example, sulphonated polystyrene resins in the H+ form. The concentration of the acid should be kept so low that an elimination of the C14-hydroxyl group and/or a splitting off of an acid-sensitive radical $R_1$ possibly present, especially a 2'-deoxyglycosyl radical, is avoided. It is preferred to use an acid concentration of 0.1 to 0.5%. In the particular case of p-toluene-sulphonic acid, there can be used a concentration thereof of 1 to 10%, based upon the amount of steroid used.

The reaction mixture can be worked up by neutralization with, for example, aqueous sodium bicarbonate or sodium carbonate solution and extraction with an organic solvent. After drying, the solvent and excess acetal can be evaporated off in a vacuum. The products can be isolated, for example, by chromatography, for example on silica gel or aluminium oxide, and/or by crystallization.

The acetalization results in the formation of a new center of asymmetry on the carbon atom of the aldehyde moiety. Thus, the new compounds of general formula (I) can be in the form of their diastereomers or also in the form of diastereomeric mixtures.

If, for example, in the case of convallatoxol or of helveticosol compounds, two adjacent hydroxyl groups in the sugar residue are in the cis configuration, these can, if desired, be temporarily protected in the usual manner. Thus, the corresponding O-acetyl compounds can be used as starting materials and, after acetalization, the acetyl radicals can be split off under basic conditions, for example with methanolic ammonia solution.

If desired, the compounds of general formula (I) can be subsequently alkylated or acylated, provided that acidic conditions do not arise which could result in the hydrolysis of the acetal grouping. On the other hand, as already mentioned, any acyl radicals possibly present can, if desired, be split off by the action of, for example methanolic ammonia solution or aqueous methanolic sodium bicarbonate solution.

The following Examples are given for the purpose of illustrating the present invention; the infra-red, ultraviolet and PMR spectra agree with the presumed structures.

EXAMPLE 1

5,19-Benzylidene-cymarol 300 mg. cymarol are dissolved in 10 ml. dioxan and mixed at ambient temperature with 1 ml. benzaldehyde diethyl acetal, as well as with 15 mg. p-toluene-sulphonic acid monohydrate. The reaction mixture is stirred for 10 minutes, then neutralized with 5% aqueous sodium bicarbonate solution and exhaustively extracted with chloroform. After working up the reaction mixture in the usual manner, the crude product obtained is purified chromatographically on 10 g. silica gel. There is obtained 5,19-benzylidene-cymarol as a thin layer chromatographically uniform, white substance, which is dissolved in benzene and precipitated therefrom by the addition of hexane. The yield is 236 mg; m.p. $150° - 155°C$.

Analysis: $C_{37}H_{50}O_9 \cdot 0.25H_2O$ (M.W. 643.3): calc.: C 69.09%; H 7.91%; O 22.80%; found: C 69.09%; H 7.81%; O 22.95%

EXAMPLE 2

5,19-Piperonylidene-cymarol

In a manner analogous to that described in Example 1, from 550 mg. cymarol and 2 ml. piperonal diethyl acetal, there are obtained 410 mg. 5,19-piperonylidene-cymarol in the form of a white, thin layer chromatographically uniform powder. After recrystallization from chloroform/petroleum ether, it has a melting point of $153°-156°C$.

Analysis: $C_{38}H_{50}O_{11} \cdot 0.5 H_2O$ (M.W. 691.8): calc.: C 65.98%; H 7.43%; O 26.58%; found: C 65.88%; H 7.45%; O 26.84%

The following compounds are prepared in an analogous manner:

5,19-benzylidene-convallatoxol
5,19-benzylidene-helveticosol
5,19-piperonylidene-convallatoxol
5,19-piperonylidene-helveticosol
3'-O-acetyl-5,19-benzylidene-helveticosol
2',3'-isopropylidene-5,19-benzylidene-convallatoxol

EXAMPLE 3

5,19-p-Chlorobenzylidene-cymarol

From 550 mg. cymarol and 2 ml. p-chlorobenzaldehyde diethyl acetal, there are obtained, in a manner analogous to that described in Example 1, 582 mg. 5,19-p-chlorobenzylidene-cymarol in the form of an amorphous, uniform powder which, after recrystallization from chloroform/pentane, melts at 148° – 155°C.

Analysis: $C_{37}H_{49}ClO_9 \cdot 0.5\ H_2O$ (M.W. 682.260): calc.: C 65.15%; H 7.39%; Cl 5.20%; O 22.27%; found: C 65.22%; H, 7.19%; Cl 5.07%; O 22.48%

The following compounds are prepared in an analogous manner:

5,19-o-chlorobenzylidene-cymarol
5,19-p-fluorobenzylidene-cymarol
5,19-(2,4-dichlorobenzylidene)-cymarol
5,19-(2-chloro-4-bromobenzylidene)-cymarol
5,19-o-methoxybenzylidene-cymarol
5,19-p-methoxybenzylidene-cymarol
5,19-p-trifluoromethylbenzylidene-cymarol
5,19-p-ethoxybenzylidene-cymarol
5,19-p-methylbenzylidene-cymarol
5,19-o-methylbenzylidene-cymarol
5,19-p-ethylbenzylidene-cymarol

EXAMPLE 4

5,19-Furfurylidene-cymarol

In a manner analogous to that described in Example 1, from 550 mg. cymarol, 2 ml. furfural diethyl acetal and 25 mg. p-toluene-sulphonic acid monohydrate in 9 ml. dioxan at 5°C., there is obtained 5,19-furfurylidene-cymarol which, after dissolving in chloroform and precipitating out with diisopropyl ether, is obtained in the form of a white, amorphous, thin layer chromatographically uniform powder, which melts at 145° – 152°C.

Analysis: $C_{35}H_{48}O_{10} \cdot 2H_2O$ (M.W. 637.8) calc.: C 65.92%; H 7.74%; O 26.34% found: 65.94%; 7.88%; 26.31%

The following compounds are obtained in an analogous manner:

5,19-pyridyl-(4)-methylene-cymarol
5,19-pyridyl-(3)-methylene-cymarol
5,19-pyridyl-(2)-methylene-cymarol
2′,3′-isopropylidene-5,19-furfurylidene-convallatoxol
3′-acetyl-5,19-furfurylidene-helveticosol
5,19-pyridyl-(4)-methylene-covallatoxol
5,19-pyridyl-(4)-methylene-helveticosol
5,19-thiophene-(2)-methylene-cymarol
2′,3′-isopropylidene-5,19-thiophene-(2)-methylene-convallatoxol
3′-acetyl-5,19-thiophene-(2)-methylene-helvaticosol.

The new compounds (I) have valuable pharmacological properties. In particular, they exert a positive inotropic action of broad therapeutic spectrum on the cardiac muscle of various kinds of mammals.

The positive inotropic action was determined on a guinea pig ventricle preparation (cf. K. Greeff et al., Probleme der klinischen Prufung herzwirksamer Glycoside, pub. Darmstadt, 1968, p. 200 et seq.). Contraction amplitudes and heart beat frequencies were recorded on a direct recorder by means of wire strain gauges. The test substance was diffused into the bath through an infusion pump at a uniform rate. As a measure for the therapeutic spectrum, there can be used the therapeutic index V (in mol./l.), which is calculated from:

$$V = C_2 - C_1$$

wherein $C_1$ is the concentration at the commencement of the increase of the contraction amplitude and $C_2$ is the concentration at the onset of the decrease of amplitude.

As can be seen from the following Table I, in the case of, for example, 5,19-benzylidene-cymarol, there is a 4.5 to 7 fold increase of the therapeutic index in comparison with the known cardiac glycosides.

TABLE I

Comparison of the therapeutic indices V

| test compound | V [M/l] | Vo/V |
|---|---|---|
| 5,19-benzylidene-cymarol | $4.46 \times 10^{-6}$ (= Vo) | 1 |
| cymarol | $6.44 \times 10^{-7}$ | 6.9 |
| convallatoxin | $6.95 \times 10^{-7}$ | 6.4 |
| digitoxin | $7.89 \times 10^{-7}$ | 5.7 |
| digoxin | $1.00 \times 10^{-6}$ | 4.5 |

The following table II shows the relative therapeutic indices for Examples 1, 2 and 4 in relationship to Cymarol and β-Methyl-digoxin respectively.

TABLE II

| Example | Relative therapeutic index | |
| | Cyamrol = 1 | β-Methyl-digoxin = 1 |
|---|---|---|
| 1 | 7 | 4 |
| 4 | 3 | 2 |
| 2 | 5 | 3 |

The known cardiac-glycosides have mainly the disadvantage of showing only a rather low therapeutic index which means a relatively high danger of intoxication in case of an individual overdosage. The compounds of this application show a surprisingly high therapeutic index and represent, therefore, an important improvement with respect to the safety of glycoside therapy.

The new compounds according to the present invention can be administered enterally and parenterally in admixture with solid or liquid pharmaceutical diluents or carriers. As injection medium, it is preferred to use water which contains the usual additives for injection solutions, for example, stabilizing agents, solubilising agents and buffers. Additives of this kind include, for example, tartrate and citrate buffers, ethanol, complex-forming agents (for example ethylenediamine-tetraacetic acid and the non-toxic salts thereof) and high molecular weight polymers (for example liquid polyethylene oxide) for viscosity regulation. Solid carrier materials which can be used include, for example, starch, lactose, mannitol, methyl cellulose, talc, highly-dispersed silicic acids, high molecular weight fatty acids (for example stearic acid), gelatine, agar-agar, calcium phosphate, magnesium stearate, animal and vegetable fats and solid high molecular weight polymers (for example polyethylene glycols); compositions which are suitable for oral administration can, if desired, contain flavoring and/or sweetening agents.

The dosage of the pharmaceutical compositions according to the present invention depends upon the degree of severity of the disease to be treated and upon the individual glycoside requirement. For a single dose, there is recommended 0.1 to 1.0 mg. of active material.

We claim:

1. Cardenolide acetals of the formula:

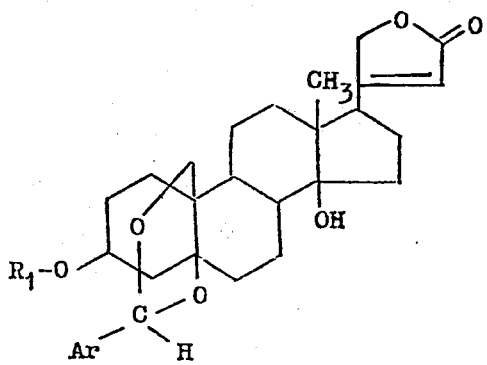

wherein $R_1$ is a glycosyl radical and Ar is a phenyl, furyl, thienyl or pyridyl radical which can be substituted by halogen atoms, alkyl or alkoxy radicals containing up to 3 carbon atoms or by trifluoromethyl, methylenedioxy or ethylenedioxy radicals.

2. Cardenolide acetals according to claim 1, wherein the substituent $R_1$ is a digitoxosyl radical of the general formula:

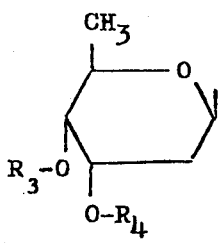

in which either $R_3$ or $R_4$ represents a hydrogen atom and the other one a hydrogen atom, a methyl radical, an acyl radical containing up to 4 carbon atoms, or $R_3$ and $R_4$ together represent an isopropylidene or lower alkoxymethylene radical.

3. Cardenolide acetals according to claim 1, wherein the substituent $R_1$ is a rhamnosyl radical of the general formula:

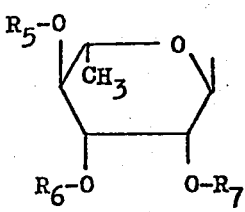

in which the symbols $R_5$, $R_6$ and $R_7$ represent hydrogen atoms or one of the symbols $R_5$, $R_6$ and $R_7$ is a methyl radical or an acyl radical containing up to 4 carbon atoms or $R_6$ and $R_7$ together represent an isopropylidene, cyclohexylidene or lower alkoxymethylene radical.

4. The compound of claim 1 which is 5,19-benzylidene-cymarol.

5. The compound of claim 1 which is 5,19-piperonylidene cymarol.

6. The compound of claim 1 which is 5,19-benzylidene-convallatoxol.

7. The compound of claim 1 which is 5,19-benzylidene-helveticosol.

8. The compound of claim 1 which is 5,19-piperonylidene-convallatoxol.

9. The compound of claim 1 which is 5,19-piperonylidene-helveticosol.

10. The compound of claim 1 which is 3'-O-Acetyl-5,19-benzylidene-helveticosol.

11. The compound of claim 1 which is 2',3'-Isopropylidene-5,19-benzylidene-convallatoxol.

12. The compound of claim 1 which is 5,19-p-chlorobenzylidene-cymarol.

13. The compound of claim 1 which is 5,19-o-chlorobenzylidene-cymarol.

14. The compound of claim 1 which is 5,19-p-fluorobenzylidene-cymarol.

15. The compound of claim 1 which is 5,19-(2,4-dichlorobenzylidene)-cymarol.

16. The compound of claim 1 which is 5,19-(2-chloro-4-bromobenzylidene)-cymarol.

17. The compound of claim 1 which is 5,19-o-methoxybenzylidene-cymarol.

18. The compound of claim 1 which is 5,19-p-methoxybenzylidene-cymarol.

19. The compound of claim 1 which is 5,19-p-trifluoromethylbenzylidene-cymarol.

20. The compound of claim 1 which is 5,19-p-ethoxybenzylidene-cymarol.

21. The compound of claim 1 which is 5,19-p-methylbenzylidene-cymarol.

22. The compound of claim 1 which is 5,19-o-methylbenzylidene-cymarol.

23. The compound of claim 1 which is 5,19-p-ethylbenzylidene-cymarol.

24. The compound of claim 1 which is 5,19-furfurylidene-cymarol.

25. The compound of claim 1 which is 5,19-pyridyl-(4)-methylene-cymarol.

26. The compound of claim 1 which is 5,19-pyridyl-(3)-methylene-cymarol.

27. The compound of claim 1 which is 5,19-pyridyl-(2)-methylene-cymarol.

28. The compound of claim 1 which is 2',3'-isopropylidene-5,19-furfurylidene-convallatoxol.

29. The compound of claim 1 which is 3'-acetyl-5,19-furfurylidene-helveticosol.

30. The compound of claim 1 which is 5,19-pyridyl-(4)-methylene-covallatoxol.

31. The compound of claim 1 which is 5,19-pyridyl-(4)-methylene-helveticosol.

32. The compound of claim 1 which is 5,19-thiophene-(2)-methylene-cymarol.

33. The compound of claim 1 which is 2',3'-isopropylidene-5,19-thiophene-(2)-methylene-convallatoxol.

34. The compound of claim 1 which is 3'-acetyl-5,19-thiophene-(2)-methylene-helveticosol.

* * * * *